United States Patent
Gärber

(10) Patent No.: US 10,285,619 B2
(45) Date of Patent: May 14, 2019

(54) ELECTRICAL IMPEDANCE TOMOGRAPHY DEVICE AND ELECTRICAL IMPEDANCE TOMOGRAPHY METHOD

(71) Applicant: Drägerwerk AG & Co. KGaA, Lübeck (DE)

(72) Inventor: Yvo Gärber, Breitenfelde (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 547 days.

(21) Appl. No.: 15/024,566

(22) PCT Filed: Sep. 24, 2014

(86) PCT No.: PCT/EP2014/002580
§ 371 (c)(1),
(2) Date: Mar. 24, 2016

(87) PCT Pub. No.: WO2015/043741
PCT Pub. Date: Apr. 2, 2015

(65) Prior Publication Data
US 2016/0235333 A1    Aug. 18, 2016

(30) Foreign Application Priority Data
Sep. 27, 2013  (EP) ..................... 13186489

(51) Int. Cl.
*A61B 5/053*    (2006.01)
*A61B 5/085*    (2006.01)
(Continued)

(52) U.S. Cl.
CPC ............ *A61B 5/0536* (2013.01); *A61B 5/004* (2013.01); *A61B 5/08* (2013.01); *A61B 5/085* (2013.01);
(Continued)

(58) Field of Classification Search
CPC ...... A61B 5/0536; A61B 5/085; A61B 5/1135
See application file for complete search history.

(56) References Cited

U.S. PATENT DOCUMENTS

| | | | |
|---|---|---|---|
| 2002/0193700 A1 | 12/2002 | Bohm et al. | |
| 2013/0002264 A1* | 1/2013 | Garber | ...................... A61B 5/08 324/600 |
| 2016/0008561 A1* | 1/2016 | Novotni | ............... A61B 5/0536 128/204.23 |

FOREIGN PATENT DOCUMENTS

EP    1 000 580 A1    5/2000

OTHER PUBLICATIONS

Gomez-Laberge C et al: "A Unified Approach for EIT Imaging of Regional Overdistension and Atelectasis in Acute Lung Injury", IEEE Transactions on Medical Imaging, IEEE Service Center, Piscataway, NJ, US, vol. 31, No. 3, Mar. 2, 2012 (Mar. 2, 2012), pp. 834-842, XP011491067, ISSN: 0278-0062, DOI: 101109/TMI .2012. 2183641 p. 835, col. 2, line 15—p. 836, col. 1, line 47 p. 837, lines 15-19 figures 2(a), 2(b).

(Continued)

*Primary Examiner* — Meredith Weare
(74) *Attorney, Agent, or Firm* — McGlew and Tuttle, P.C.

(57) ABSTRACT

An electrical impedance tomography device includes a plurality of electrodes, a display apparatus, and a control and evaluation unit for reconstructing a matrix of image elements, a spatial distribution of impedance changes in an electrode plane, from measurement signals with a reconstruction algorithm. A time series of matrices are provided from an inhalation and an exhalation that follow. The control unit detects a local impedance change, as a function of a quantity monotonically dependent on average alveolar pressure, as inhalation and exhalation curves from the time series of matrices, to calculate a parameter representing the deviation between the inhalation and exhalation curves as a (Continued)

dissipation value of the image element and to associate the parameter with the image element, to combine the dissipation values of all examined image elements in a dissipation map, and to display the dissipation values with graphical codings dependent on dissipation values of the dissipation map.

20 Claims, 1 Drawing Sheet

(51) Int. Cl.
     *A61B 5/00*          (2006.01)
     *A61B 5/08*          (2006.01)

(52) U.S. Cl.
     CPC .......... *A61B 5/6823* (2013.01); *A61B 5/7271* (2013.01); *A61B 5/742* (2013.01); *A61B 5/7242* (2013.01)

(56) References Cited

OTHER PUBLICATIONS

Frerichs I et al: "Regional respiratory inflation and deflation pressure volume curves determined by electrical impedance tomography; Regional respiratory inflation and deflation pressure-volume curves determined by electrical impedance tomography", Physiological Measurement, Institute of Physics Publishing, Bristol, GB, vol. 34, No. 6, May 29, 2013 (May 29, 2013), pp. 567-577, XP020245474, ISSN: 0967-3334, DOI: 101088/0967-3334/34/6/567 p. 568, line 34—p. 570, line 20; figures 1-3.
International Search Report dated Dec. 17, 2014.

\* cited by examiner

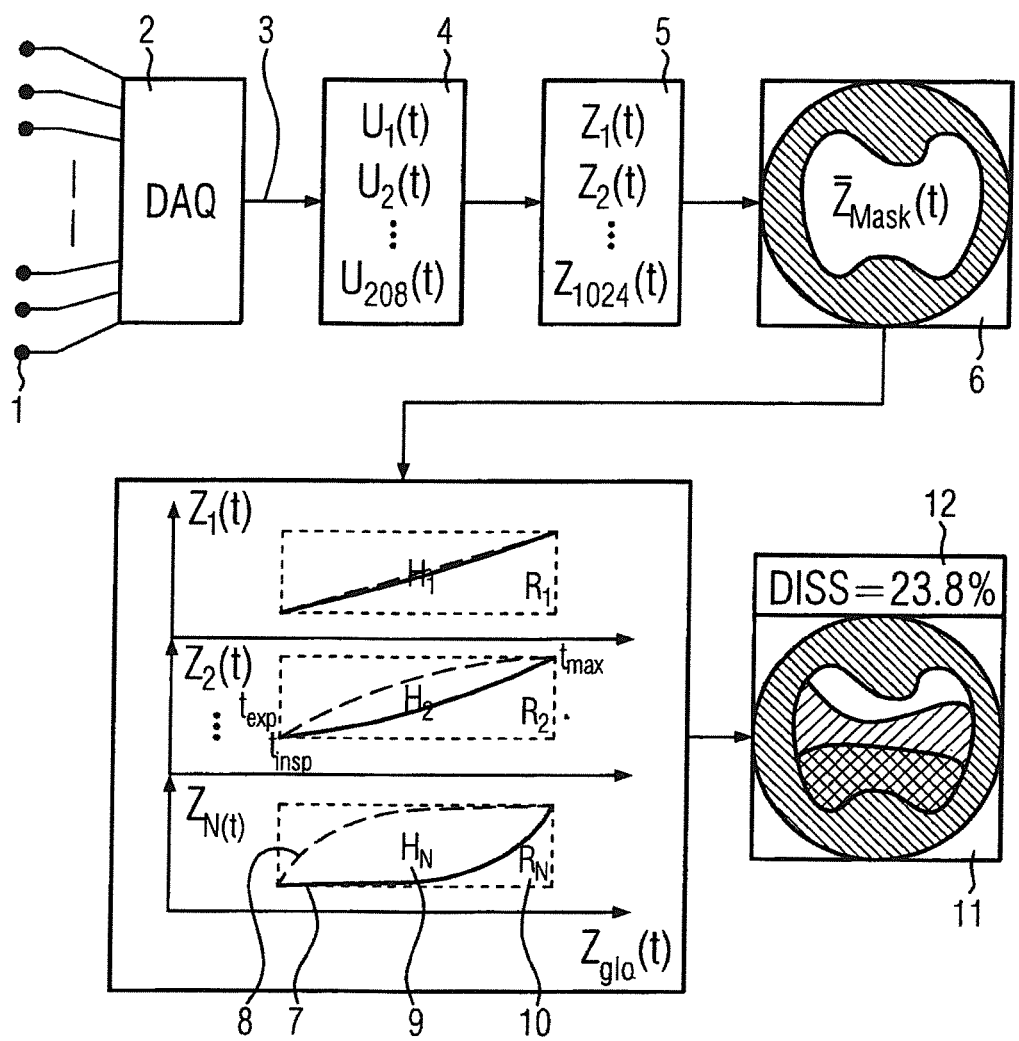

ELECTRICAL IMPEDANCE TOMOGRAPHY DEVICE AND ELECTRICAL IMPEDANCE TOMOGRAPHY METHOD

CROSS REFERENCE TO RELATED APPLICATIONS

This application is a United States National Phase Application of International Application PCT/EP2014/002580 filed Sep. 24, 2014 and claims the benefit of priority under 35 U.S.C. § 119 of European Patent Application 13 186 489.4 filed Sep. 27, 2013, the entire contents of which are incorporated herein by reference.

FIELD OF THE INVENTION

The present invention pertains to an electrical impedance tomography device with a plurality of electrodes, which can be placed around the thorax of a patient and define an electrode plane; with a display device and with a control and analysis unit, which is connected to the electrodes and is set up by programming to supply at least one electrode pair as a feeding electrode pair with an alternating current or with an alternating voltage, to record a voltage signal or current signal each as a measured signal with a plurality of the remaining electrode pairs and to let other electrode pairs act consecutively as feeding electrode pairs in order to reconstruct from the measured signals with a reconstruction algorithm a matrix of image elements, which matrix represents a spatial distribution of the impedance changes in the electrode plane, and to repeatedly record measured signals over at least one inhalation and at least one exhalation, which follow each other, and to reconstruct matrices in order to obtain a time series of matrices with impedance changes of the image elements over the at least one inhalation and the at least one exhalation.

BACKGROUND OF THE INVENTION

Such an electrical impedance tomography device (EIT device) is known, for example, from EP 1 000 580 A1, which is used to record an "electrical impedance tomogram" of the cross section of the thorax of a patient.

Electrical impedance tomography is a method for the reconstruction of impedance distributions, more precisely impedance changes relative to a reference distribution, in electrically conductive bodies. A plurality of electrodes are placed for this on the surface of the body to be examined. A ring-shaped equidistance array of 16 electrodes, which can be placed around the thorax of a patient with a belt, is used in typical cases.

The control and analysis unit has analog electrical circuits for signal amplification and for feeding alternating current and electronic circuits for digitizing and preprocessing the voltage signals as well as a digital signal processor for controlling the device and for processing the recorded data for reconstructing the impedance distribution. The control and analysis unit ensures that one pair each of (preferably) adjacent electrodes is supplied with an alternating electric current (e.g., 5 mA at 50 kHz) and the electric voltages are detected on a plurality of remaining electrode pairs by the control and analysis unit (it is also possible, in principle, conversely to feed an alternating voltage to an electrode pair and to measure the alternating currents over a plurality of remaining electrode pairs); the voltages of all remaining pairs of adjacent electrodes are typically detected, but it is also possible, in principle, to skip individual electrodes, as a result of which information will, however, be lost. The impedance distribution, more precisely, the change in the impedance distribution compared to a reference distribution (e.g., the impedance distribution during the first recording), can be reconstructed with algorithms from the totality of all measured signals during the consecutive current feeds, during which the position of the feeding electrode pair migrates around the electrode ring step by step. The prior-art algorithms yield as the result of the reconstruction a matrix of 32×32 image elements, and the matrix contains for each image element the reconstructed impedance change for this image element. A plurality of such matrices are recorded at preset time intervals during at least one inhalation and at least one exhalation, e.g., over one breath with inhalation and an exhalation following it. These are displayed on a display device consecutively, as a result of which the intratidal time course of the impedance change is made visible practically as a film.

Thoracic electrical impedance tomography for measuring the regional lung ventilation has been increasingly used in intensive care medicine focused on research. Theoretical models and experimental comparisons of EIT with CT images of the thorax show a nearly complete proportionality of the air content in the lung tissue and the impedance of the latter. The breaths are resolved spatially with about 20% of the thoracic diameter and in time typically with about 20 to about 40 matrices per second, which makes possible a bed-side monitoring of the regional lung ventilation. The matrices are occasionally also called images of the impedance distribution (with 32×32=1024 image elements) or frames.

Consequently, a sequence of impedance changes, which is also called here a time series of impedance change values for the given image element, is determined for each image element over one phase of inhalation or one phase of exhalation. The terms time series of impedance change values and impedance change curves will hereinafter be used synonymously, even though a time series comprising discrete points is not a curve in the strict sense of the word. The time series are also represented in the form of curves as functions of time in the diagrams for reasons of representation.

An essential advantage of the high frame rate is that the breaths, especially the phase of inhalation and the phase of exhalation of the breath, can be resolved over time. Therefore, it is possible not only to analyze not only the regional distribution of the ventilated air in the end-inspiratory state (tidal image), but also to investigate the course over time during the inhalation and exhalation in order to infer regional lung mechanical processes therefrom. For example, the behavior of the local impedance change curves is thus examined compared to the global impedance change curve in the article "New Methods for Improving the Imaging Quality in Functional EIT Tomograms of the Lungs," G. Kühnel et al., Biomed. Tech. (Berlin), 42 (1997), Suppl. 470-1, but the difference in behavior during inhalation and exhalation was not taken into account, but a "filling capacity," which is a variable related to the tidal image, was determined from the slope of a fitted straight line (this would have to be explained somewhat more accurately). Local inhalation curves are determined in the article "Regional Ventilation Delay Index: Detection of Tidal Recruitment Using Electric Impedance Tomography," T. Muders et al., Vincent J. L., ed., Yearbook of Intensive Care and Emergency Medicine, and the time at which the local inhalation curve reaches 40% of its maximum is related to the global inhalation time for each local inhalation curve, and an image of faster or slower regions with lower or higher time constants than the average is generated from this. A "regional ventilation delay index (RVD)" is defined from this as an indicator of the inhomogeneity over time.

However, none of the methods simultaneously takes into account the inhalation curve and the exhalation curve and consequently nor the amount of work of breathing dissipated at the alveolar level. The work of breathing at the alveolar level is almost completely stored in the ideal case elastically by the expansion of the alveoli and of the thorax during the inhalation and the stored energy is released again passively during the exhalation. There is no hysteresis in this case between inhalation and exhalation. This is true, of course, at the alveolar level only. If the normal breathing pressure is measured at the mouthpiece or at the upper bronchi, a hysteresis is obtained already because of the volume-dependent frictional losses of the air flow in the airways. These can be estimated and calculated by fitting the data to motion equations of breathing mechanical models.

A simple breathing mechanical model in mechanical ventilation, in which the lungs are considered to be a compartment with frictional resistance of the flexible tube and of the airways R and with the system compliance C, ignoring losses due to inertia and turbulence as well as the diaphragmatic pressure, leads to the motion equation:

$$p_0(t) = R(V)\frac{dV}{dt} + \frac{V(t)}{C(p)} = p_R(t) + p_{alv}(t).$$

Here, $V(t)$ is the respirated air volume and $p_0(t)$ is the upper airway pressure. The first term $p_R(t)$ is the pressure drop due to friction at the airways, while the second term $p_{alv}(t)$ can be interpreted as the mean alveolar pressure (mean alveolar pressure means here averaged over all alveoli, and this mean alveolar pressure over the breath is a function of time).

In healthy lungs, the compliance C can be assumed to be constant, i.e., independent from the pressure in case of small differences in pressures between inhalation and exhalation. Thus, the volume is linearly dependent in this model on the mean alveolar pressure $p_{alv}(t)$, which is, in turn, proportional to the global impedance change (the sum of all local impedance changes of the individual image elements is called the global impedance change here). Therefore, there should not be any hysteresis between the alveolar pressure $p_{alv}(t)$ and the volume curve $V(t)$ and hence relative to the global impedance change curve $Z_{glo}(t)$ (however, there is a hysteresis, in general, between the volume $V(t)$ and the airway pressure $p_0(t)$).

In case of spatially and temporally homogeneous lungs, this should also be true of the local impedance change curves (i.e., the impedance change in a pixel in the image plane), i.e., there should not be any hysteresis between the mean alveolar pressure $p_{alv}(t)$ and the local impedance change curves. If, however, some of the alveoli no longer work in the purely elastic range, an alveolar p-V hysteresis will develop there.

SUMMARY OF THE INVENTION

An object of the present invention is to provide an electrical impedance tomography device and a corresponding method, with which the local alveolar pressure-volume hysteresis and hence the dissipated alveolar work of breathing or a variable proportional thereto can be locally detected and this can be represented, resolved in space, in a visually detectable and simple manner.

Provisions are made according to the present invention for the control and analysis unit to be set up (configured) to analyze the time series of the matrices in order to detect the local impedance change over the at least one inhalation and the at least one exhalation for each image element or a selected set of image elements (e.g., a selected image area) as a function of a variable strictly monotonically dependent on the mean alveolar pressure as a local inhalation curve and local exhalation curve. The variable against which these inhalation and exhalation curves are considered to be plotted may be the mean alveolar pressure itself, a linear function thereof or a function dependent on it strictly monotonically, the latter implying that any change in the mean alveolar pressure leads as a consequence to a change in the variable being considered in an unambiguous direction. In other words, there is a reversibly unambiguous image of the mean alveolar pressure relative to the variable that is dependent on it strictly monotonically; this is, of course, especially true of a linearly dependent variable.

Even though the time series of the local impedance changes comprises discrete value pairs in the coordinate system defined by said variables, these may also be connected in some sections by straight sections or by fitting preset functions to a curve, however. The impedance change curves are detected as local inhalation and exhalation curves for the examined image elements (these may be all image elements or even only image elements from selected image areas).

The local impedance change curves are, in general, closed, because the lungs again return to the same state in terms of pressure and volume after an inhalation and an exhalation. The local impedance change curves run in a diagram, one coordinate axis of which corresponds to the volume and the other one is a strictly monotonic function of the pressure and is especially proportional thereto, so that there is a kind of P-V diagram for each image element. The inhalation curve component and the exhalation curve component of the impedance change curve coincide as straight lines in the ideal case of a completely elastic lung area. However, non-elastic losses ensure, in the general case, that the inhalation curve component and the exhalation curve component do not coincide but enclose a hysteresis area. The control and analysis unit is set up, furthermore, to calculate as the local dissipation value of the image element for a respective parameter representing the deviation between the local inhalation curve and the local exhalation curve. The control and analysis unit is set up, furthermore, to associate with image elements their local dissipation values or dissipation values obtained therefrom by standardization, to combine the dissipation values into a dissipation map, in which graphic codings dependent on the local dissipation values thereof are associated with the image elements, and to display the dissipation map in the image plane defined by the electrode plane on the display device.

The inhalation and exhalation curves of each examined image element are detected in a preferred embodiment as closed curves, which are called hysteresis areas in the non-elastic case (analogously to closed curves in case of magnetization). The control and analysis unit is set up, furthermore, in this embodiment to calculate the area located between the inhalation curve component and the exhalation curve component as a hysteresis area of the image element as the parameter representing the deviation between the inhalation curve and the exhalation curve, to associate with each examined image element the hysteresis area thereof as a dissipation value or as a dissipation value obtained therefrom by standardization, and to combine these into a dissipation map, in which a graphic coding dependent on the hysteresis value of each image element is associated with each image element, and to display the hysteresis map of the image plane on the display device.

One advantage of displaying a dissipation map is the rapid detectability of losses of regional alveolar work of breathing during a complete breath, because both the local inhalation curve component and local exhalation curve component of the local impedance change curves are used. Since the mechanical energy is stored, as a rule, elastically, as in the case of healthy alveoli, losses of alveolar work of breathing are indicative of non-elastic disturbances during breathing, which may develop in case of diseased lungs and/or if the parameters of a ventilator are not set optimally.

For example, the value of the difference of the integrals of the inhalation curve and the exhalation curve over the two common argument areas could be used as another example of a parameter representing the deviation between the inhalation curve and the exhalation curve; this area between the curves yields a parameter characterizing the deviation in the case of non-closed curves and corresponds to the hysteresis area in case of closed curves.

Provisions are made in an advantageous embodiment for the local impedance change curves of all examined image elements of the lung cross section to be standardized with a common factor such that the sum of all standardized local impedance change curves is equal to an independently determined volume curve of the respiration. As a result, the standardized local impedance change curves can be interpreted as volume curves. The independently determined volume curve of respiration can be provided, for example, by a ventilator, which performs a mechanical ventilation of the patient.

The variable, which is strictly monotonically dependent on the mean alveolar pressure and is used by the control and analysis unit, can be determined by the control and analysis unit in different ways. In a preferred embodiment, the control and analysis unit receives independently determined pressure and volume curves of respiration and determines from them the mean alveolar pressure by means of a breathing mechanical model and uses the mean alveolar pressure itself as said variable. This may be performed, for example, by square minimization with respect to the parameters R and C from the above motion equation, the pressure and volume curves of respiration, $p_0(t)$ and $V(t)$, originating from a ventilator mechanically ventilating the patient. The variable that is strictly monotonically dependent on the mean alveolar pressure is a variable depending on it linearly in this case.

As an alternative, the control and analysis unit may be set up to use an independently determined volume curve of respiration, which is a linear function of the mean alveolar pressure during a hypothetical elastic deformation, as a variable that is linearly dependent on the mean alveolar pressure (and is consequently also dependent strictly monotonically). The independently determined volume curve may originate, in turn, from a ventilator.

In another alternative embodiment, the control and analysis unit may be set up, furthermore, to use as the variable that is strictly monotonically dependent on the mean alveolar pressure a variable that is linearly dependent on it in the form of the global impedance change curve, which is determined from the sum of all local impedance change curves and is proportional to the volume curve of respiration and thus to the curve of the mean alveolar pressure during a hypothetical elastic deformation.

In a preferred embodiment, the control and analysis unit may be set up to standardize the variable that is strictly monotonically dependent on the mean alveolar pressure such that this is equal to the end-expiratory pressure (PEEP) at the end of exhalation and is equal to the maximum inhalation pressure (PMAX) at the end of the inhalation, so that the local impedance change curves are given as pressure-volume (p-V) curves.

In an alternative embodiment, the control and analysis unit may be set up to standardize the hysteresis areas by dividing each hysteresis area by the product of the difference between the end-expiratory values of the local impedance curve and the difference between the end-expiratory values of the variable that is proportional to the mean alveolar pressure, so that standardized hysteresis areas are obtained between 0 (no hysteresis) and 1 (maximum hysteresis). This shows clearly that the smallest rectangle enclosing the hysteresis curve (with the sides of the rectangle being parallel to the coordinate axes) is placed around the hysteresis curve and the area occupied by the hysteresis curve is divided by the area of the rectangle placed around it. In the ideally elastic case, the area of the hysteresis curve is 0 and the standardized hysteresis value is thus 0. In the opposite extreme limit case, the hysteresis curve follows the straight shape of the rectangle, so that the hysteresis area and the area of the rectangle are equal and an extreme hysteresis value of 1 is obtained.

In a preferred embodiment, the control and analysis unit can be set up to assign a sign with each, possibly standardized hysteresis area by checking whether the exhalation curve component of the local impedance change curve is, as a function of the variable proportional to the mean alveolar pressure, above the inhalation curve component and by assigning the sign + if so and by assigning the sign – if not. The assignment of the sign may also be performed in the reversed manner.

The control and analysis unit may be set up to display the dissipation map with the graphic coding of the hysteresis values in the form of a color or gray value scale on the display device.

The control and analysis unit may be set up to form an averaged dissipation map either by detecting and averaging the local impedance change curves for each examined image element over a plurality of breaths and determining the dissipation map on the basis of the averaged local impedance change curves or by averaging the dissipation maps of a plurality of breaths and displaying the averaged dissipation map.

In an advantageous embodiment, the control and analysis unit may be set up to associate a global alveolar dissipation value with a dissipation map by averaging the values and the amounts thereof, adding up these or by determining the maximum of all values or amounts of the dissipation map and to display this alveolar dissipation value numerically or graphically on the display device.

The present invention comprises, furthermore, a method for recording a sequence of EIT images of a cross-sectional plane of the thorax of a patient by a plurality of electrodes, which are distributed over the circumference of the thorax and define an electrode plane, wherein one electrode pair is supplied in the method as a feeding electrode pair with an alternating current or an alternating voltage, voltage signals or current signals are recorded as measured signals from a plurality of the other electrode pairs and other electrode pairs of the plurality of electrode pairs are consecutively operated as feeding electrode pairs, a matrix of image elements, which represents the distribution of the impedance changes from one image element to the next image element in the electrode plane, is reconstructed from the totality of the measured signals with a reconstruction algorithm, matrices of the impedance change are repeatedly reconstructed over time in order to obtain a time series of matrices of the local impedance changes over at least one inhalation and at least one exhalation, which follow one another. The local impedance change is detected from the time series of the matrices for each image element or for a selected set of examined image elements as a function of a variable that is strictly monotonically dependent on the alveolar pressure over at least one inhalation and at least one exhalation as a local inhalation curve and local exhalation curve. A parameter representing the deviation between the local inhalation curve and the local exhalation curve is calculated as a local dissipation value, the local dissipation values of all examined image elements are combined into a dissipation map, in which a graphic coding that is dependent on their dissipation value is assigned to the image elements, and the dissipation map in the image plane that is defined by the electrode plane is displayed on the display device.

The at least one inhalation and the at least one exhalation, which are being examined in connection with the present invention and which follow each other, are typically a breath with an inhalation and with an exhalation following it. However, it is also possible, in principle, to begin first with an exhalation and to consider the inhalation following it; further inhalations and exhalations may, in principle, also be included in the analysis.

The present invention will be explained below on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic block diagram of an electrical impedance tomography device.

DESCRIPTION OF THE PREFERRED EMBODIMENTS

For example, a 16-electrode system is used in the EIT device shown schematically as a block diagram in FIG. 1, and the electrodes 1 may be arranged in a ring-shaped manner around the thorax. Current is fed by means of the data acquisition unit 2 of the EIT device via a pair of (preferably) adjacent electrodes, voltage measurements are performed over a plurality of the other adjacent electrode pairs, then current is fed via another pair of adjacent electrodes, etc., until a plurality of or all adjacent electrode pairs acted as feeding electrode pair once; the measured voltages obtained in the process are also called frames. A frame of measured voltages consists of 208 voltage values here, which can be recorded at frame rates between 10 Hz and 50 Hz. The number of 208 measured voltages is obtained in case of a 16-electrode system when each of the 16 pairs of adjacent electrodes is used once as a feeding electrode pair, and there are 13 different pairs of adjacent electrodes, between which a measured voltage is detected, among the 14 remaining electrodes, so that a total of 16×13=208 measured voltages are detected during one pass. This is a typical mode of actuation for an EIT device with a 16-electrode system. It is, however, also conceivable in technical implementations of EIT devices that not all of the electrodes present are used to feed current or voltage, but individual electrodes or electrode pairs are jumped over during the feeding. It is likewise conceivable that voltage measurements or current measurements are not performed on all of the electrodes present, but individual electrodes or electrode pairs are jumped over and left out during the measurements.

The 208 time series of the voltages $u_1(t), u_2(t), \ldots, u_{208}(t)$ sent in this exemplary embodiment to the memory unit 4 of the EIT device or to an external memory unit via a bus system 3. 1024 (relative) impedance changes $Z_1(t), Z_2(t), \ldots, Z_{1024}(t)$, which are imaged on an image with 32×32 image elements, are reconstructed from the measured voltages. The reconstruction and further analyses may be performed both online and offline, displaced in space and time. The data generated below can therefore be stored internally in the EIT system via a bus system or in an external memory. No distinction will be made below any more between the two possibilities.

A calculation module reconstructs the 1024 time series of the relative impedance changes $Z_1(t), Z_2(t), \ldots, Z_{1024}(t)$ from the 208 time series of the voltages $u_1(t), u_2(t), \ldots, u_{208}(t)$ and makes them available in a local impedance module 5. Only the information-carrying "ventilated" image elements (pixels) i=[1, 2, ..., N] are selected with a preset image element mask 9 or an image element mask 9 determined from the data, i.e., the marginal areas 6 indicated in FIG. 1 are masked out.

A global impedance change $Z_{glo}(t)$ is determined by adding up the local impedance changes over all information-carrying image elements. This global impedance change curve $Z_{glo}(t)$ is proportional to the respirated volume and is consequently also a variable dependent linearly on the mean alveolar pressure and is consequently also a strictly monotonically dependent variable.

$Z_{glo}(t)$ is used here as the variable representing the mean alveolar pressure (and being strictly monotonically dependent on it). FIG. 1 shows as an example the local impedance change curves of three image elements as a function of $Z_{glo}(t)$. The inhalation curve 7 is shown as a solid line and the exhalation curve as a broken line. The hysteresis area 9, which is standardized here for each image element by determining the smallest rectangle 10 completely enclosing the inhalation and exhalation curves 7 and 8 and then dividing the hysteresis area $H_i$ of the i-th image element by the area $R_i$ of the smallest circumscribed rectangle, is located between this inhalation curve 7 and the exhalation curve 8.

The use of the global impedance change curve as the variable representing the mean alveolar pressure and the standardization of the hysteresis areas by the enclosing rectangular area to calculate the dissipation values has the advantage that such a dissipation map can also be determined without the knowledge of independently determined pressure and volume curves, e.g., from a ventilator. Since the result of the respective dissipation values is a relative variable related to itself, areas with a smaller ventilation component are treated by the standardization in this definition equivalently to areas with a high ventilation component, because precisely alveolar lung areas with poor ventilation may work inelastically in case of disease.

The global impedance change curve $Z_{glo}(t)$ of the breath is generated by adding up all N local impedance change curves $Z_i(t)$ within the pixel mask, where N is the number of examined image elements within the pixel mask:

$$Z_{glo}(t) = \frac{1}{N}\sum_{i=1}^{N} Z_i(t).$$

To avoid a bias, the image element just analyzed may also be removed from the averaging. Only the dependence of the local impedance change curve $Z_i(t)$ of the image element i currently being analyzed on the global impedance change curve $Z_{glo}(t)$ is examined for the phase of inhalation between the start of inhalation $t_{insp}$ and the end of inhalation at $t_{max}$ as curve $Z_i^{insp}(Z_{glo}(t))$ and for the phase of exhalation between the start at $t_{max}$ and the end at $t_{exp}$ as curve $Z_i^{esp}(Z_{glo}(t))$ for all examined image elements i within the pixel mask.

The signed hysteresis area $H_i$ for each image element i is obtained as $$H_i = \int_{z_{glo}(t_{exp})}^{z_{glo}(t_{max})} Z_i^{exp}(Z_{glo})dZ_{glo} - \int_{z_{glo}(t_{insp})}^{z_{glo}(t_{max})} Z_i^{insp}(Z_{glo})dZ_{glo}$$

$$\forall\, i \in \{1, 2 \ldots, N\}$$

The smallest enclosing rectangular area for each image element i is obtained as:

$$R_i = (\max(Z_i) - \min(Z_i)) \cdot (\max(Z_{glo}) - \min(Z_{glo})) \quad \forall i \in \{1, 2 \ldots, N\}$$

The standardized hysteresis area $$D_i = \frac{H_i}{R_i} \cdot 100\%$$

$$\forall\, i \in \{1, 2 \ldots, N\}$$

is defined as the dissipation value of the image element i of the dissipation map. The dissipation values will now be in the range of −100% to +100% and can be represented on the display device 11 in a color-coded manner.

There is hardly any hysteresis in case of $D_i$ values having a low amount around 0% and the alveoli work in the elastic range, as is shown, e.g., in the graphs $Z_1(t)$ in FIG. 1. $D_i$ values of, for example, above 50%, as they are shown in the lower of the three graphs for $Z_N(t)$ in FIG. 1, are indicative of a high percentage of dissipative losses of work due to non-elastic effects. The interpretation is not so clear for greater negative $D_i$ values. Image elements with such values usually belong to the class of the non-ventilated image elements and may suggest fluid shifting.

A global dissipation value is defined as a scalar variable from the local dissipation values of the individual image elements by averaging over the dissipation map:

$$DISS = \frac{1}{N}\sum_{i=1}^{N} D_i.$$

While specific embodiments of the invention have been shown and described in detail to illustrate the application of the principles of the invention, it will be understood that the invention may be embodied otherwise without departing from such principles.

The invention claimed is:

1. An electrical impedance tomography device comprising:
    a plurality of electrodes, which can be placed around a thorax of a patient and define an electrode plane;
    a display device; and
    a control and analysis unit, which is connected to the electrodes and is configured by programming to:
    supply at least one electrode pair as a feeding electrode pair with an alternating current or with an alternating voltage;
    record a voltage signal or current signal as measured signals with a plurality of other electrode pairs from the plurality of electrodes, with other electrode pairs of the plurality of electrode pairs acting consecutively as feeding electrode pairs in order to reconstruct a matrix of image elements, which represents a spatial distribution of impedance changes in the electrode plane, from the measured signals with a reconstruction algorithm, and to repeatedly record measured signals over at least one inhalation and at least one exhalation, which follow each other, and to reconstruct matrices in order to obtain a time series of matrices with impedance changes of the image elements over the at least one inhalation and the at least one exhalation;
    detect local impedance changes as a function of a variable, which variable is strictly monotonically dependent on a mean alveolar pressure, over the at least one inhalation as a local inhalation impedance change curve and over the at least one exhalation as a local exhalation impedance change curve from the time series of the matrices with the impedance changes of the image elements or from a selected set of the impedance changes of image elements;
    calculate a respective parameter representing a deviation between the local inhalation impedance change curve and the local exhalation impedance change curve as a local dissipation value;
    associate respective image elements with local dissipation values or local dissipation values obtained therefrom by standardization;
    combine the local dissipation values of all examined image elements into a dissipation map in an image plane defined by the electrode plane, in which dissipation map graphic coadings dependent on the local dissipation values of the image elements are associated with said image elements; and
    display the dissipation map of the image plane on the display device.

2. An electrical impedance tomography device in accordance with claim 1, wherein the control and analysis unit is furthermore configured to detect the inhalation curve and the exhalation curve of each examined image element as closed curves and to calculate a hysteresis area enclosed by the closed curves as a dissipation value of the image element.

3. An electrical impedance tomography device in accordance with claim 2, wherein the control and analysis unit is furthermore configured to standardize the hysteresis areas into hysteresis values by dividing each hysteresis area by a product of a difference between end-respiratory values of the local impedance curve and a difference between end-respiratory values of the variable proportional to the mean alveolar pressure, so that standardized hysteresis areas are obtained between 0 (no hysteresis) and 1 (maximum hysteresis).

4. An electrical impedance tomography device in accordance with claim 2, wherein the control and analysis unit is furthermore configured to assign a sign to each, possibly standardized hysteresis area by checking whether an exhalation curve component of the local impedance change curve as a function of the variable proportional to the mean alveolar pressure is above the inhalation curve component and if so, either a + sign or a − sign is assigned, and the opposite sign is assigned if not.

5. An electrical impedance tomography device in accordance with claim 1, wherein the control and analysis unit is, furthermore configured to standardize the local impedance change curves of all image elements with a common factor such that the sum of all standardized local impedance change curves is equal to an independently determined volume curve of respiration.

6. An electrical impedance tomography device in accordance with claim 1, wherein the control and analysis unit is furthermore configured to determine the mean alveolar pressure from independently determined pressure and volume curves of respiration with a breathing mechanical model and to use the breathing mechanical model determined mean alveolar pressure as the variable that is strictly monotonically dependent on the mean alveolar pressure.

7. An electrical impedance tomography device in accordance with claim 1, wherein the control and analysis unit is furthermore configured to use as the variable, that is strictly monotonically dependent on the mean alveolar pressure, a variable that is linearly dependent on the mean alveolar pressure in the form of an independently determined volume curve of the respiration, which independently determined volume curve of the respiration is a linear function of the mean alveolar pressure in case of a hypothetical elastic deformation.

8. An electrical impedance tomography device in accordance with claim 1, wherein the control and analysis unit is furthermore configured to use as the variable, that is strictly monotonically dependent on the mean alveolar pressure, a variable that is linearly dependent on the mean alveolar pressure in the form of a global impedance change curve, which global impedance change curve is determined from a sum of all local impedance change curves and which global impedance change curve is proportional to a volume curve of the respiration and hence proportional to a curve of the mean alveolar pressure in case of a hypothetical elastic deformation.

9. An electrical impedance tomography device in accordance with claim 1, wherein the control and analysis unit is furthermore configured to standardize the variable that is strictly monotonically dependent on the mean alveolar pressure such that the standardized variable is equal to an end-expiratory pressure (PEEP) at an end of the exhalation and is equal to the maximum inspiratory pressure (PMAX) at an end of the inhalation, so that the local impedance change curves represent pressure-volume (p-V) curves.

10. An electrical impedance tomography device in accordance with claim 1, wherein the control and analysis unit is furthermore configured to display the dissipation map with the graphic coding in the form of a color value scale or a gray value scale on the display device.

11. An electrical impedance tomography device in accordance with claim 1, wherein the control and analysis unit is furthermore configured to form an averaged dissipation map either by detecting and averaging the local impedance change curves over a plurality of breaths for each image element and determining the dissipation map on the basis of the averaged local impedance change curves or by averaging the dissipation maps of several breaths, and displaying the averaged dissipation map.

12. An electrical impedance tomography device in accordance with claim 1, wherein the control and analysis unit is furthermore configured to associate a global alveolar dissipation value with a dissipation map by averaging, adding up or by determining a maxima of all values or amounts from the dissipation map and displaying this global alveolar dissipation value numerically or graphically on the display device.

13. A method for recording a sequence of electrical impedance tomography images of a cross-sectional plane of a thorax of a patient, the method comprising the steps of:
providing an electrical impedance tomography device comprising a plurality of electrodes, which can be placed around the thorax of a patient and define an electrode plane, a display device; and a control and analysis unit, which is connected to the electrodes;
with the electrical impedance tomography device, supplying one electrode pair, as a feeding electrode pair, with an alternating current or with an alternating voltage, and recording voltage signals or current signals as measured signals with a plurality of the other electrode pairs and other electrode pairs of the plurality of electrode pairs are consecutively operated as feeding electrode pairs;
with the control and analysis unit, reconstructing a matrix of image elements, which represents a spatial distribution of the impedance changes for one image element to the next image element in the electrode plane, from a totality of the measured signals with a reconstruction algorithm; and
with the control and analysis unit, repeatedly reconstructing matrices of the impedance change over time in order to obtain a time series of matrices of the local impedance changes over at least one inhalation and at least one exhalation, which follow each other;
with the control and analysis unit, detecting a respective local impedance change from the time series of the matrices for each image element or a selected set of image elements as a function of a variable that is strictly monotonically dependent on a mean alveolar pressure over the at least one inhalation as a local inhalation impedance change curve and over the at least one exhalation as a local exhalation impedance change curve; and
with the control and analysis unit, calculating a parameter representing the deviation between the local inhalation impedance change curve and the local exhalation impedance change curve as a local dissipation value;
with the control and analysis unit, combining the local dissipation values of all examined image elements into a dissipation map in an image plane defined by the electrode plane, in which a graphic coding dependent on a local dissipation value is associated with each examined image element; and
displaying the dissipation map of the image plane on the display device.

14. A method in accordance with claim 13, further comprising, with the control and analysis unit, detecting the inhalation curve and the exhalation curve of each examined image element as closed curves and calculating a hysteresis area enclosed by the closed curves as a dissipation value of the image element.

15. A method in accordance with claim 14, further comprising, with the control and analysis unit, standardizing the hysteresis areas into hysteresis values by dividing each hysteresis area by a product of a difference between end-respiratory values of the local impedance curve and a difference between end-respiratory values of the variable proportional to the mean alveolar pressure, so that standardized hysteresis areas are obtained between 0 (no hysteresis) and 1 (maximum hysteresis).

16. A method in accordance with claim 13, further comprising, with the control and analysis unit, standardizing the local impedance change curves of all image elements with a common factor such that the sum of all standardized local impedance change curves is equal to an independently determined volume curve of respiration.

17. A method in accordance with claim 13, further comprising, with the control and analysis unit, determining the mean alveolar pressure from independently determined pressure and volume curves of respiration with a breathing mechanical model and using the breathing mechanical model determined mean alveolar pressure as the variable that is strictly monotonically dependent on the mean alveolar pressure.

18. A method in accordance with claim 13, further comprising, with the control and analysis unit, using as the variable that is strictly monotonically dependent on the mean alveolar pressure a variable that is linearly dependent on the mean alveolar pressure in the form of an independently determined volume curve of the respiration, which independently determined volume curve of the respiration is a linear function of the mean alveolar pressure in case of a hypothetical elastic deformation.

19. A method in accordance with claim 13, further comprising, with the control and analysis unit, using as the variable that is strictly monotonically dependent on the mean alveolar pressure a variable that is linearly dependent on the mean alveolar pressure in the form of the global impedance change curve, which global impedance change curve is determined from a sum of all local impedance change curves and which is proportional to a volume curve of the respiration and hence proportional to a curve of the mean alveolar pressure in case of a hypothetical elastic deformation.

20. A method in accordance with claim 13, further comprising, with the control and analysis unit, standardizing the variable that is strictly monotonically dependent on the mean alveolar pressure such that the standardized variable is equal to an end-expiratory pressure (PEEP) at the end of the exhalation and is equal to the maximum inspiratory pressure (PMAX) at the end of the inhalation, so that the local impedance change curves represent pressure-volume (p-V) curves.

* * * * *